(12) United States Patent
Tritschler et al.

(10) Patent No.: US 11,369,761 B2
(45) Date of Patent: Jun. 28, 2022

(54) PUMP CAP FOR A PHARMACEUTICAL CONTAINER, INSERT FOR A PUMP CAP FOR A PHARMACEUTICAL CONTAINER, PHARMACEUTICAL CONTAINER WITH THE PUMP CAP, AND COMPUTER PROGRAM PRODUCT

(71) Applicant: MEDA AB, Solna (SE)

(72) Inventors: Hans-Jurgen Tritschler, Munich (DE); Mario Weingart, Dresden (DE); Joachim Maus, Muhlheim (DE)

(73) Assignee: MEDA AB

( * ) Notice: Subject to any disclaimer, the term of this patent is extended or adjusted under 35 U.S.C. 154(b) by 686 days.

(21) Appl. No.: 15/577,418

(22) PCT Filed: Mar. 2, 2016

(86) PCT No.: PCT/EP2016/054350
§ 371 (c)(1),
(2) Date: Mar. 15, 2018

(87) PCT Pub. No.: WO2016/155970
PCT Pub. Date: Oct. 6, 2016

(65) Prior Publication Data
US 2019/0366020 A1    Dec. 5, 2019

(30) Foreign Application Priority Data
Mar. 30, 2015    (DE) ..................... 10 2015 004 073.1

(51) Int. Cl.
*G08B 1/08*       (2006.01)
*A61M 15/08*      (2006.01)
(Continued)

(52) U.S. Cl.
CPC ............ *A61M 15/08* (2013.01); *A61J 7/0427* (2015.05); *A61M 11/006* (2014.02);
(Continued)

(58) Field of Classification Search
CPC ............... A61M 15/08; A61M 11/006; A61M 2205/18; A61M 2205/3561;
(Continued)

(56) References Cited

U.S. PATENT DOCUMENTS 7,151,456 B2 * 12/2006 Godfrey ........... G06K 19/07758
340/573.1
8,109,414 B2    2/2012 Cater et al.
(Continued)

FOREIGN PATENT DOCUMENTS

CN        103201185 B      7/2013
DE      102008064559 A1    4/2010
(Continued)

*Primary Examiner* — Toan N Pham (57) ABSTRACT

In a pump cap for a pharmaceutical container, there is an electronic unit adapted to record activation of the pump cap by a user for the release of the contents of the container and release the reporting signals in a wireless manner, and to enable operational energy to come from outside, via an appliance in the form of a personal digital assistant, in a wireless manner, in order to record one or several pump cap activations by a user and the wireless release of the reporting signals from one or more pump cap activations.

19 Claims, 4 Drawing Sheets

(51) Int. Cl.
| | |
|---|---|
| *A61M 11/00* | (2006.01) |
| *A61J 7/04* | (2006.01) |
| *G08B 21/24* | (2006.01) |
| *G08B 25/10* | (2006.01) |
| *B05B 12/00* | (2018.01) |
| *A61J 1/05* | (2006.01) |
| *B05B 11/00* | (2006.01) |
| *G08B 21/18* | (2006.01) |
| *G08B 25/00* | (2006.01) |
| *B05B 12/02* | (2006.01) |

(52) U.S. Cl.
CPC ............ *B05B 12/008* (2013.01); *G08B 21/24* (2013.01); *G08B 25/10* (2013.01); *A61J 1/05* (2013.01); *A61J 2200/30* (2013.01); *A61J 2205/60* (2013.01); *A61M 2205/18* (2013.01); *A61M 2205/3561* (2013.01); *A61M 2205/3592* (2013.01); *B05B 11/308* (2013.01); *B05B 12/02* (2013.01); *G08B 21/182* (2013.01); *G08B 25/009* (2013.01)

(58) Field of Classification Search
CPC ......... A61M 2205/3592; B05B 12/008; B05B 12/02; B05B 11/308; B05B 11/30; G08B 25/10; G08B 21/24; G08B 21/182; G08B 25/009; A61J 7/0427; A61J 2200/30; A61J 2205/60; A61J 1/05
See application file for complete search history.

(56) References Cited

U.S. PATENT DOCUMENTS

| | | | |
|---|---|---|---|
| 8,710,958 | B2 | 4/2014 | Yang et al. |
| 8,807,131 | B1 | 8/2014 | Tunnell et al. |
| 9,346,200 | B2 | 5/2016 | Desoto-Burt et al. |
| 10,238,282 | B2 * | 3/2019 | Voss ...................... A61F 9/0008 |
| 2005/0251289 | A1 * | 11/2005 | Bonney ............. A61M 15/0083 |
| | | | 700/244 |
| 2006/0157749 | A1 * | 7/2006 | Okuno .................. H01L 29/785 |
| | | | 257/288 |
| 2010/0018524 | A1 * | 1/2010 | Jinks ................. A61M 15/009 |
| | | | 128/200.23 |
| 2011/0041845 | A1 | 2/2011 | Solomon et al. |
| 2012/0080029 | A1 | 4/2012 | Koerner et al. |
| 2014/0155827 | A1 * | 6/2014 | Ostrander ............. A61M 5/002 |
| | | | 604/111 |
| 2015/0061867 | A1 | 3/2015 | Engelhard et al. |
| 2017/0136178 | A1 | 5/2017 | Kamen et al. |

FOREIGN PATENT DOCUMENTS

| | | |
|---|---|---|
| DE | 102010042007 B4 | 4/2013 |
| JP | 2011-527658 A | 11/2011 |
| KR | 20120128060 A | 11/2012 |
| RU | 2510758 C2 | 4/2014 |
| WO | 2014106056 A2 | 4/2012 |
| WO | 2014068504 A2 | 5/2014 |

\* cited by examiner

PUMP CAP FOR A PHARMACEUTICAL CONTAINER, INSERT FOR A PUMP CAP FOR A PHARMACEUTICAL CONTAINER, PHARMACEUTICAL CONTAINER WITH THE PUMP CAP, AND COMPUTER PROGRAM PRODUCT

TECHNICAL FIELD, PRIOR ART, TECHNOLOGICAL BACKGROUND

The following is a description of a pump cap for a pharmaceutical container, an inlay for a pump cap for a pharmaceutical container with a pump cap and a computer program product that serves the pump cap jointly with an electronic unit.

Examples of administered, nasally and sublingually, controlled substances from a container are the well known, various and costly aerosol metering valves and spray pumps by Aptar Pharma, for example (www.aptar.com).

Recording the discharge processes of such pharmaceutical dispensers can help count the number of discharge processes. The patient or the doctor can thus be provided with an overview of the discharge processes that were carried out. In this regard, DE 10 2010 042 007 A1 and DE 10 2008 064 559 A1 are also referred to as technological background.

From DE 10 2014 204 939 B3, a dispenser in the shape of an MDI (Metered Dose Inhaler) for discharging a pharmaceutical medium is popular. This dispenser has a sensor to record a discharge process and an electronic processing circuit to record and further process one of the signals emitted from the sensor. The sensor is part of a sensor unit, which has a radio transmitter to produce a radio signal and the processing circuit has a radio receiver adapted to receive radio signals produced from the radio transmitter.

Two electronic components are thus intended for this dispenser, which are integrated in a joint dispenser but are not galvanically coupled to each other. Instead, both electronic components, the sensor unit and the processing circuit are connected via a radio interface. This processing circuit has an energy source (battery or accumulator) that stores the radio receiver and display device in a specific location in a dispenser and, if applicable, a storage device to save the discharge processes, taking into consideration the time of the discharge process. The sensor unit has a sensor, a radio transmitter and, if applicable, an energy source (battery and accumulator) for operating the radio transmitter. Instead of the energy source, a converter is intended to convert mechanical energy to electrical energy, which is identical with the sensor. The user thus uses it to convert the energy created by the discharge process into electrical energy for the radio transmitter. A piezoelectric generator serves as a converter.

Underlying Problem

This arrangement has a string of disadvantages, of which only a few are mentioned here. It is a separate, receiving unit of a pharmaceutical container to be additionally purchased by the user (the patient). It makes the medication container to be carried by the patient bigger. Its operation is also conceptually very expensive. On one hand, the signal and energy producing piezoelectric generator is expensive. On the other hand, the arrangement of batteries and an display in the processing circuit located in the dispenser are also to be disposed of after the life span of the arrangement.

Solution to Problem

In order to at least partially solve the previously mentioned problems, a pump cap for a pharmaceutical container, an inlay for a pump cap for a pharmaceutical container with a pump cap and a computer program product for a personal digital assistant is suggested.

There is an electronic unit in the pump cap. This electronic unit is adapted, on one hand, to record the activation of a pump cap by a user to release the content of the container and, on the other hand, to release the reporting signals of the activations of the pump cap in a wireless manner, in order to allow the required operational energy to be led from outside in a wireless manner for the record of activations and release of signals.

The operational energy of the electronic unit will be transmitted from an electronic unit, independent of the pump cap, in the form of a so-called personal digital assistant (PDA), such as a mobile or cordless phone, a so-called smart phone, a so-called smart watch, a tablet computer, a notebook or something similar; the electronic unit is adapted to receive the operational energy of the personal digital assistant.

Advantages, Designs

The pharmaceutical container with this kind of adapted pump cover is essentially less costly in production and thus also in disposal. The electronic unit with a pharmaceutical container comprising approximately 100 to 200 medications, independent of the pump cap, has a longer life and operational cycle than a pharmaceutical container with a pump cap. The costly disposable part of the discharge unit of DE 10 2014 204 939 B3 with batteries and an display is thus omitted. What's more, it is, nevertheless, common for a user these days to move around with such a person digital assistant (PDA) at all times. Likewise, a patient who has to administer nasal and sublingual controlled (pharmaceutical) substances carries this pharmaceutical container about as a rule. As long as the user avoids the solution suggested here in terms of carrying unnecessary electronic appliances i.e. he passes on the pump cap on the pharmaceutical container on the processing circuits with batteries and accumulators suggested here, the radio receiver and the MDI display device of DE 10 2014 204 939 B3. Furthermore, the expensive cost-intensive piezoelectrical generator is omitted.

The electronic appliance, namely the personal digital assistant, has, on one hand, corresponding structural components in the form of one or several antennae or other emitters such as the associated control electronics and a processor with storage and input/output elements (touch-sensitive display panels). A computer program product is suggested for the processor of the personal digital assistant (a so-called app), which allows the control electronics of the antenna to release operational energy for the electronic unit of the pump cover in order to receive the signals released from the electronic unit in a wireless manner and, after their processing, to have the processor display the pump cap activations on the display of the electronic appliance.

The electronic unit of the pump cap is a transmitter, for example in the form of a RFID-Module (RFID=Radio Frequency Identification) and essentially has a chip module comprising an antenna designed as a coil or dipole. This chip module enables the contactless, automated registration and/or retrieval of data in/out of the chip of a transmitter. Such a transmitter comprises, for example, a coil-shaped transmitter antenna next to the chip, which enables data access. A pump cap personalization, explained in detail, is part of the registered data, more precisely relating to the pharmaceutical container, with regards to "pairing" with the computer program product of the personal digital assistant. The signals reported by the pump cap activations are part of the retrieved data.

The transmitter, thus the antenna and chip module, is integrated in the pump cap and receives its operational energy from the personal digital assistant (PDA) only if the user activates the corresponding computer program product on the personal digital assistant, or, permanently, as long as the pump cap on the pharmaceutical container is sufficiently close to the personal digital assistant and radiates energy via its corresponding antenna(e).

In a variant, the transmitter is adapted to transmit data via Near Field Communication (=NFC) via radio and within a short distance of approximately 10 cm to 20 cm. Details in this regard are also explained in ISO/IEC 14443 A and B or in ISO/IEC 15693. Data for the NFC Communication is thus transmitted at a 13.56 MHz range. In this regard, active and passive NFC transformers can be used. Active NFC transmitters are able to initiate and communicate connections. Passive NFC transmitters are not able to build connections independently. They need an active partner, in this case the PDA, to test the data.

Active transmitters need a source of energy whilst the passive transmitter can manage without a source of energy. In order to state their information via the pumping operation(s), passive transmitters make use of the energy transferred from active readers. Energy is transferred to the transmitter via the active reader, in order to transmit information about the pumping operation(s) within a short distance of around 10 cm to 20 cm. In a variant, the operation energy storage of the transmitter is meant to be assigned, for example, in the form of a capacitor.

Since a diversity of smart phones (Apple 6, Android, BlackBerry, Windows, etc) is being planned or already exists, those equipped with NFC functionality (according to NFC-Standard ISO/IEC 14443 A and B or ISO/IEC 15693), namely coils, control electronics, appropriate NFC-control software (NFC protocol stack) in the processor-operational system of the Smart phone, the inlay/electronic unit of the pump cap in different smart phones or other personal digital assistants PDA are supplied with operational energy to respond and retrieve. Such a personal digital assistant is used for the collaboration of the pump cap described here and/or the inlay described below.

Instead of a Near-Field Communication, (energy and) data transmission can also occur via Bluetooth Standard, Wibree Standard, ANT+-Standard or Zigbee Standard.

In a variant, the electronic unit of a pump cap is equipped with a sensor comprising a switch adapted to record a discharge process. This switch can be built in a particularly simple form through two electrical contacts that are electrically bridged to the opening of the pharmaceutical container via a metallic, for example aluminum, capsule if the user presses down the pump cover to cause a discharge process. If the cap of the pharmaceutical container is designed without a metal capsule, then the switch simply has an opening or closing switch. Aside from this switch sensor, a capacitive, magnetic or other form of recording can be used to ensure that the electronic unit is capable of releasing an appropriate signal.

In an additional variant, an inlay in a pharmaceutical container is suggested, wherein the electronic unit is a transmitter. The transmitter comprises essentially a chip module comprising an antenna designed as a coil or dipole for the contactless, automated registration and/or retrieval of data in and out of the chip, wherein the registered data comprises a personalized identifier for pairing the electronic unit with a computer program product in the personal digital assistant (PDA) and/or the retrieved data comprise the signals reported by the activation of the pump covers.

The inlay comprises plastic wrap, whose outside diameter is smaller than the inside diameter of the pump cap. The inlay is shaped in a way that it is inserted and, if applicable, stuck into the pump cap to ensure that it is accommodated between the opening of the pharmaceutical container and one located at the pump operation toward the fixed pharmaceutical container wall and the pump cap. The plastic wrap of the inlay has an opening passage for a drug discharge socket. The plastic wrap carries the chip module of the transmitter and its antenna, which is equipped as a planar ring coil or dipole. In this variant, the electronic unit is also equipped with a sensor with a switch adapted for recording the discharge process. This switch can be built in a particularly simple form through two electrical contacts that are electrically bridged to the opening of the pharmaceutical container via a metallic, for example aluminum, capsule if the user presses down the pump cover to cause a discharge process. If the opening of the pharmaceutical container is designed without a metal capsule, then the switch simply has an opening or closing switch. Otherwise, capacitive, magnetic or other types of sensor systems are appropriate to record one or several occurring discharge processes. The discharge process is then transmitted via the transmitter to the personal digital assistant.

Foil material for the inlay can be wood-free paper, coating paper or paper stuffed with resin, synthetic and/or plastic foil from plastic material such as Polyethylene (PE), Polyvinyl chloride (PVC), Polyvinyl chloride-Acetate-Copolymer, Polyethylene terephthalate (PET) or Polyethylene terephthalate glycol-modified (PETG), Polyethylene naphthalate (PEN), Acrylonitrile-Butadiene-Styrene-Copolymers (ABS), Polyvinyl butyral (PVB), Polymethyl-methacrylate (PMMA), Polyimide (PI), Polyvinyl alcohol (PVA), Polystyrene (PS), Polyvinyl phenol (PVP), Polyethylene (PE), Polypropylene (PP), Polycarbonate (PC) or their foil derivatives with a thickness of at least 75 µm or more. One or multiple layers of the support structure can be produced from this foil material in which one or several multi-layer spiral or cylindrical coil can be produced as antenna coil for Near-Field Communication. Furthermore, a capacitor can be included to store the operational energy received via the antenna coil in such single or multi-layer support structures.

A shape (diameter and height) of a 1 Euro coin is thus produced for the inlay, for example, with a central passage opening (a few millimeters of the diameter or the lateral dimension) for the drug discharge socket of the pharmaceutical container.

This inlay is particularly advantageous provided it can be used in the readily conceived container from pump caps and pharmaceutical containers prior to final assembly without any modification carried out on the pump cap or the pharmaceutical container. Through the small construction height, which is derived from the thickness of the foil materials and chips as well as the sensor arrangement, the actuation path of the pump cap also does not undergo any practical change to ensure that the discharge volume of the medication during the activation of the pump cap also does not vary with the figure in the inlay located in the pump cap.

In one aspect an assembly is provided, comprising (i) a pharmaceutical container comprising a nasal spray, for example in the form of a solution or suspension, preferably Dymista® nasal spray (an azelastine HCl/Fluticasone propionate combination), (ii) a pump cap connected to a drug discharge socket of the pharmaceutical container, and (iii) an electronic unit, which is either accepted in an insert provided between the pharmaceutical container and the pump cap, or directly in said pump cap. Here, the pump cap can be realized with the electronic unit and/or the insert provided between the pharmaceutical container and the pump cap in the variants described above.

In another aspect, a computer program product is provided for the personal digital assistant PDA, which is adapted and programmed so that an electronic unit is supplied in an inlay or, directly in a pump cap according to one of the previous claims by an appropriate control of the personal digital assistant PDA with operating energy and discharge processes from the pharmaceutical container is detected, comprising a preparation mode in order to implement a pairing of a respective electronic unit in an inlay in the pump cap or directly in a pump cap with a personal digital assistant, a wake-up mode in order to activate the electronic unit in the inlay and/or in the pump cap, a receiving mode in order to wait for the user to activate the pump cap so that the electronic unit transmits signals which reflect the discharge processes from the pharmaceutical container by activating the pump cap, an evaluation mode in order to measure the time elapsed between successive activations of the pump cap and to categorize different events based on the time elapsed.

Additional details are also defined in the dependent claims.

BRIEF DESCRIPTION OF THE DRAWINGS

Additional goals, features, advantages, and potential applications are discernible from the following description of design examples with reference to the corresponding drawings, which shall not be considered limiting in any way. Here, all features described and/or illustrated by images show per se or in arbitrary combinations thereof the objective disclosed here, regardless of their grouping in the claims or their reference. The dimensions and proportions of the components shown in the figures are not necessarily true to scale here; in order to implement a design; they may deviate from the illustration.

DETAILED DESCRIPTION OF THE DRAWINGS

Figure 1:
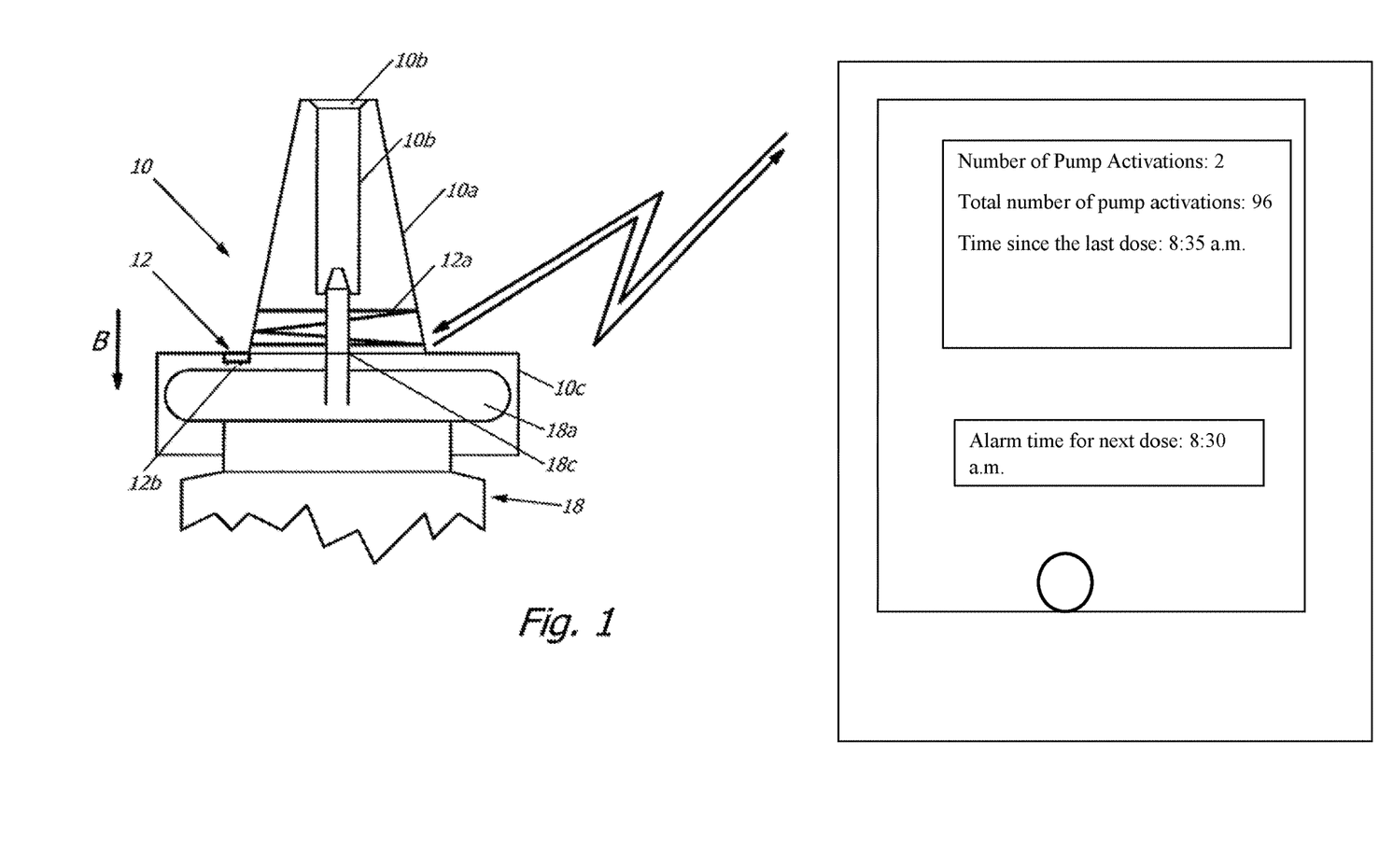
FIG. 1 shows a variant of the pump cap in a schematic, lateral cross-section in cooperation with a computer program executed on a personal digital assistant PDA.

FIG. 1 shows a first design of a pump cap 10 made from plastic for a pharmaceutical container 18. This pump cap 10 is designed as an attachment for the pharmaceutical container 18. For this purpose, the pump cap 10 comprises an applicator socket 10a, which conically tapers towards it free end. The applicator socket 10a extends away from a seat 10c showing a constant radius arch, which is designed to accept the pharmaceutical container 18. This pharmaceutical container 18 comprises a fluid reservoir, not shown in greater detail, a metal, for example aluminum, capsule 18a, closing the neck of the pharmaceutical container 18, and an outlet socket 18b. The metal capsule 18a and the outlet socket 18b can be displaced in reference to each other. Here, the pharmaceutical container 18 is designed such that by pushing down the seat 10c showing a constant radius arch, the pump cap 10 is pressed in the direction towards the metal capsule 18a of the outlet socket 18b into the neck of the pharmaceutical container 18, and here a defined volume of the pharmaceutical medium, previously located in the liquid reservoir of the pharmaceutical container 18, is discharged through the outlet socket 24.

The outlet socket 24 is accepted in an outlet channel 10b allocated to the applicator socket 10a. The seat 10c with a constant radius arch shows a cover disk and a tubular section. The tubular section is open at one (lower) end and encompasses the neck and perhaps partially the upper section of the pharmaceutical container 18. The cover disk of the seat 10c with a constant radius arch closes the tubular section at its other (upper) end and is pressed for discharging the pharmaceutical medium in the direction towards the metal capsule 18a of the pharmaceutical container 18.

An electronic unit 12 is allocated to the pump cap 10. Said cap in turn is adapted to detect any activation of the pump cap 10 by the user in reference to the pharmaceutical container 18, in order to discharge the content of the container. Furthermore, the electronic unit 12 is adapted to wirelessly transmit signals reflecting such activations of the pump cap 10. Finally, the electronic unit 12 is adapted to be wirelessly supplied with operating energy from the outside using an electronic device, here a personal digital assistant PDA for (i) detecting one or more actuations of the pump cap 10 by a user and for (ii) wirelessly transmitting signals regarding one or more activation(s) of the pump cap 10.

Figures 1A, 3:
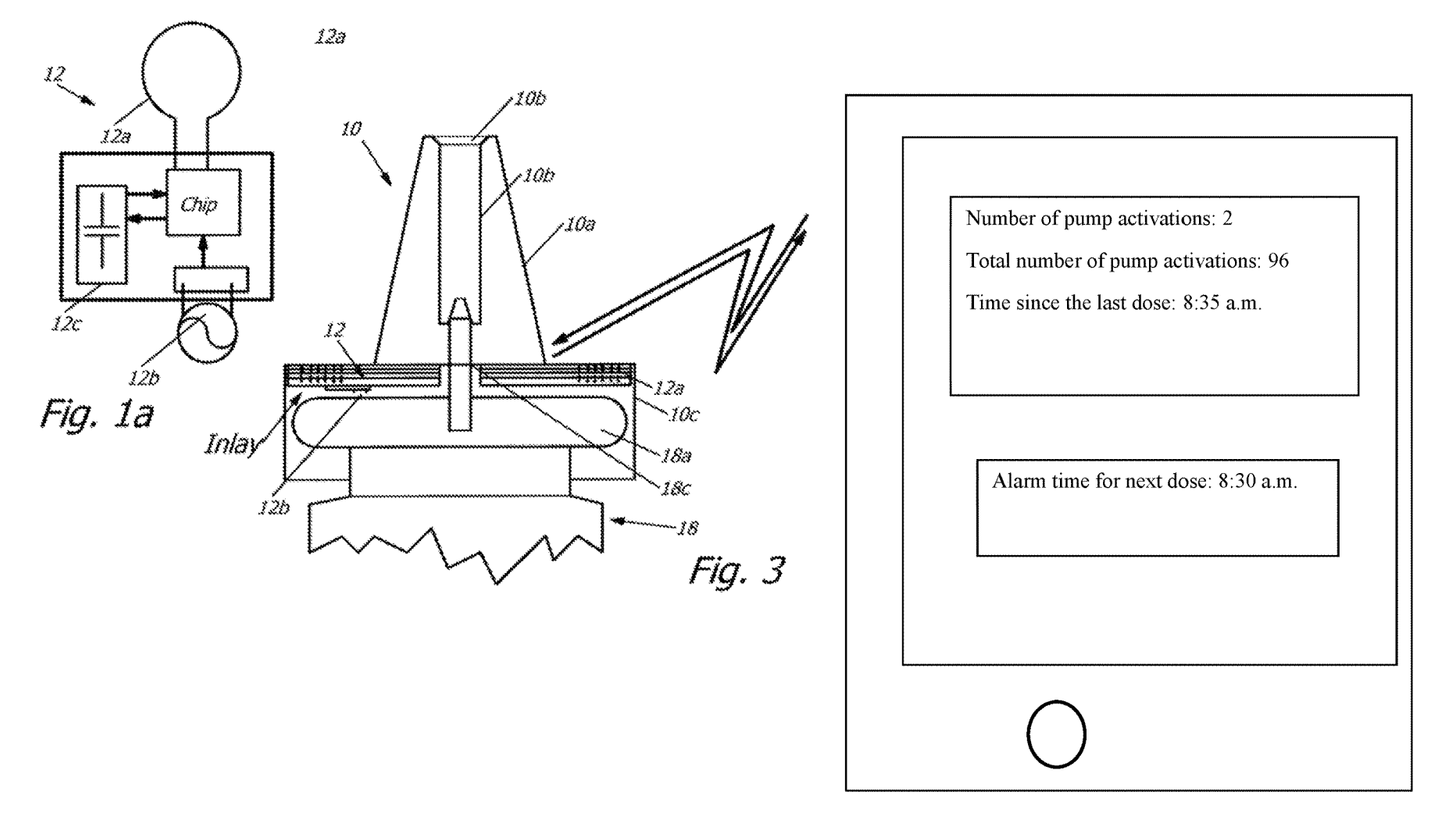
FIG. 1a shows a variant of an electronic unit for the pump cap with a transmitter and an antenna 12a designed as a coil in a schematic illustration.
FIG. 3 shows another variant of a pump cap in a schematic lateral cross-section in cooperation with a computer program product executed on a personal digital assistant.

As also illustrated in FIG. 1a, the electronic unit 12 includes a transmitter, which essentially comprises a chip module and an antenna 12a designed as a coil or as a dipole. The electronic unit 12 is adapted for the wireless, automatic registering and/or retrieval of the data in/out of the chip. The data to be entered includes, for example, a personal identification to pair the electronic unit 12 with a computer program product on the personal digital assistant PDA. This way it is ensured that a pharmaceutical container 18, more precisely its pump cap/its electronic unit 12, communicates exclusively the pump processes to be counted to the computer program product on the personal digital assistant of a user of the pharmaceutical container 18. The data to be read from the electronic unit 12 includes the signals reflecting the activation of the pump cap 10. This data telegram to be transmitted can additionally include the personal identifications written during the pairing of the computer program product on the personal digital assistant PDA of the respective user in the electronic unit 12.

Via the antenna 12a, designed in FIG. 1a as a coil, the electromagnetic energy received by the antenna 12a, transmitted by the personal digital assistant PDA, can be collected in the electronic unit 12 via an energy generation circuit and saved as electric energy in the operating energy storage unit 12c here realized as a capacitor. This way, the electric energy is available for subsequent energy supply of the chip module when transmitting the signals reflecting the actuation of the pump cap 10 (perhaps in the data telegram including the personalized identification).

In the variant of FIG. 1 the electronic unit 12 of the transmitter is integrated in the pump cap. The transmitter is adapted to only receive operating energy from the personal digital assistant when the user of the respective computer program product is activated on the personal digital assistant PDA. In this case, the PDA emits the energy via an appropriate antenna. Alternatively, the transmitter and/or its electronic unit 12 are adapted to permanently receive operating energy from the personal digital assistant PDA as long as the pump cap 10 is located on the pharmaceutical container 18 in a sufficient spatial proximity of the personal digital assistant PDA and this PDA emits via appropriate antenna(e) energy to the antenna 12*a* of the electronic unit 12.

The electronic unit 12 is equipped with a sensor 12*b*, which shows in one variant a switch adapted for recording an output process. This switch can be formed in a particularly simple form by two electric contacts, which are electrically bridged by a metal capsule 18*a* to close the pharmaceutical container 18 when the user pushes the pump cap 10 down to such an extent that a discharge process occurs. If the closure of the pharmaceutical container 18 was to be performed without any metal capsule 18*a*, for example designed by an electrically non-conductive plastic, the sensor 12*b* may represent a switch designed as a simple opening or closing switch sensor. Instead of this switch, here a capacitive, magnetic, or other sensor 12*b* may also be provided for detecting the pumping process so that the electronic unit 12 can emit a signal to the personal digital assistant PDA, respectively representing the discharge process.

For the electronic unit 12, such NFC-components of the companies NXP (www.nxp.com) or AMS (www.ams.com) may be used for example, respectively comprising a signal input, in order to record and process sensor signals, and to allow transmitting them via the antenna 12*a* to the personal digital assistant PDA.

In the variant illustrated in FIG. 1, the antenna 12*a* is embedded in the plastic material of the applicator socket 10*a* of the pump cap 10. Here, the coil antenna 12*a* designed as a loop shows several windings, which taper following the cone of the applicator socket 10*a*. In other variants, not shown here, the coil antenna 12*a* may also be accepted in the seat 10*c* with a constant radius arch, for example in the cover disk of the seat 10*c* with a constant radius arch or its tubular section.

Figures 2, 2A:
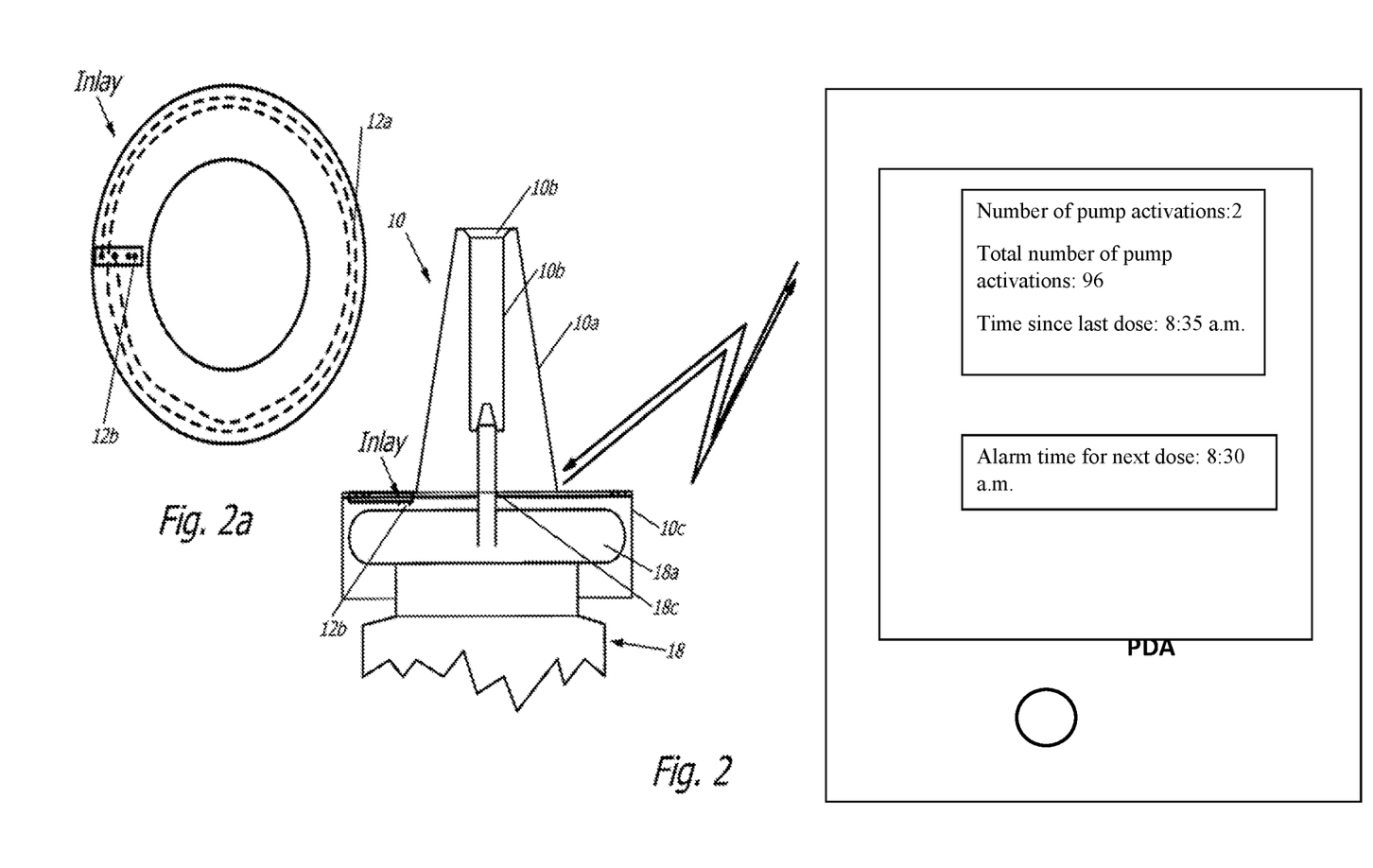
FIG. 2 shows another variant of a pump cap in a schematic lateral cross-section in cooperation with a computer program product executed on a personal digital assistant.
FIG. 2a shows a variant of an electronic unit for the pump cap with a transmitter and an antenna designed as a coil in a schematic top view.

In the variant shown in FIGS. 2 and 3, the electronic unit 12 is not embedded in the plastic material of the pump cap 10. Rather, here the electronic unit 12 is a part of a separate insert in the form of an inlay for the pump cap 10 of a pharmaceutical container 18 that can be produced independently from the pump cap 10.

The tubular section of the pump cap 10 is open at one (lower) end and encompasses the neck and perhaps partially the upper section of the pharmaceutical container 18. The cover disk of the seat 10*c* with a constant radius arch closes the tubular section at its other (upper) end and is pressed in the direction towards the metal cap 18*a* of the pharmaceutical container 18 in order to discharge the pharmaceutical medium. The inlay is located at the interior wall of the cover disk of the seat 10*c* with a constant radius arch, for example adhered or fastened by way of spot welding. This inlay also shown in FIG. 2*a* shows a circular disk-shaped form with the diametric dimensions of approximately a 1-Euro coin, here with a round, central penetrating opening (showing a few millimeters in diameter or lateral dimension) for the drug discharge socket 18*c* of the pharmaceutical container 18.

The inlay carries the electronic unit 12 at the side (in FIG. 2 at the bottom) facing the pharmaceutical container 18. Similar to the variant of FIG. 1, it is equipped with a sensor 12*b*, which in one variant shows a switch adapted to detect a discharge process. This switch can be formed in a particularly simple design by two electric contact sites, which are then electrically bridged by a metal capsule 18*a* for closing the pharmaceutical container 18 when the user pushes the pump cap 10 down to such an extent that a discharge process occurs. If the closure of the pharmaceutical container 18 is designed without a metal capsule 18*a*, for example made from an electrically not conducting plastic, the sensor 12*b* may represent a switch simply designed as an opening or closing switch. Instead of this switch sensor, here a capacitive, magnetic, or other sensor 12*b* may also be provided for detecting a pumping process, so that the electronic unit 12 can transmit to the personal digital assistant PDA a signal appropriately reflecting the drug discharge process.

Otherwise, the electronic unit 12 is consistent with the variant described in the context with FIGS. 1 and 1*a*. The plastic material of the insert represents, in the variant of FIG. 2, a layer of plastic film, for example made from plastic, such as polyethylene (PE) or polyvinyl chloride (PVC) with a thickness of approximately 100 µm. The antenna 12*a*, here designed as a coil antenna, is applied on this plastic film and contacts the electronic unit 12, which comprises also the sensor 12*b*.

In the variant of FIG. 3, unlike in the variant of FIG. 2, the inlay is designed in several layers, with the plastic material of the inlay in the variant of FIG. 3 representing several laminated layers of synthetic film, for example plastics such as polyethylene (PE) or polyvinyl chloride (PVC) showing a thickness of 75 µm. The windings of the coil antenna 12*a* are located between the individual layers. In this stack of plastic films, in one variant, in addition to the antenna 12*a* also the operating energy storage unit 12*c* is located. With regards to sizing and design of the coil antenna 12*a* in its different variants discussed above, reference is made for example to "Antenna Circuit Design for RFID Applications", AN710, Youbok Lee, Ph.D., 2003 Microchip Technology Inc. Another literature source for sizing and design of the coil antenna 12*a*, also dependent on the various different RFID-chips that can be inserted in the electronic unit, is "RFID Design Fundamentals and Applications", Albert Lozano-Nieto, CRC Press Taylor & Francis Group 6000 Broken Sound Parkway NW, Suite 300 Boca Raton, Fla. 33487-2742, ©2011 by Taylor and Francis Group, LLC. Another example of literature for sizing and design of the coil antenna 12*a* is "Design of Antennas for RFID Application", Ming-Tao Zhang et al. in "Development and Implementation of RFID Technology" edited by Cristina TURCU, ISBN 978-3-902613-54-7, pp. 554, February 2009, I-Tech, Vienna, Austria.

The pump cap with the corresponding electronic unit 12 according to FIG. 1, or the pump cap 10 with an inlay according to FIGS. 2 and 3, is combined with a pharmaceutical container 18 to form another container, and a nasal spray is located in the pharmaceutical container, for example in the form of a solution or suspension, preferably Dymista® nasal spray, a combination of azelastine hydrochloride and Fluticasone propionate, with 1 g suspension comprising 1,000 microgram azelastine hydrochloride and 365 microgram fluticasone propionate, and with one jet of 0.14 g comprising 137 microgram azelastine hydrochloride and 50 microgram fluticasone propionate, and with the other components of the nasal spray representing disodium edetate, glycerol, micro-crystalline cellulose, and carmellose sodium, polysorbate 80, benzalconium chloride, phenylethyl alcohol, and purified water.

Figure 4:
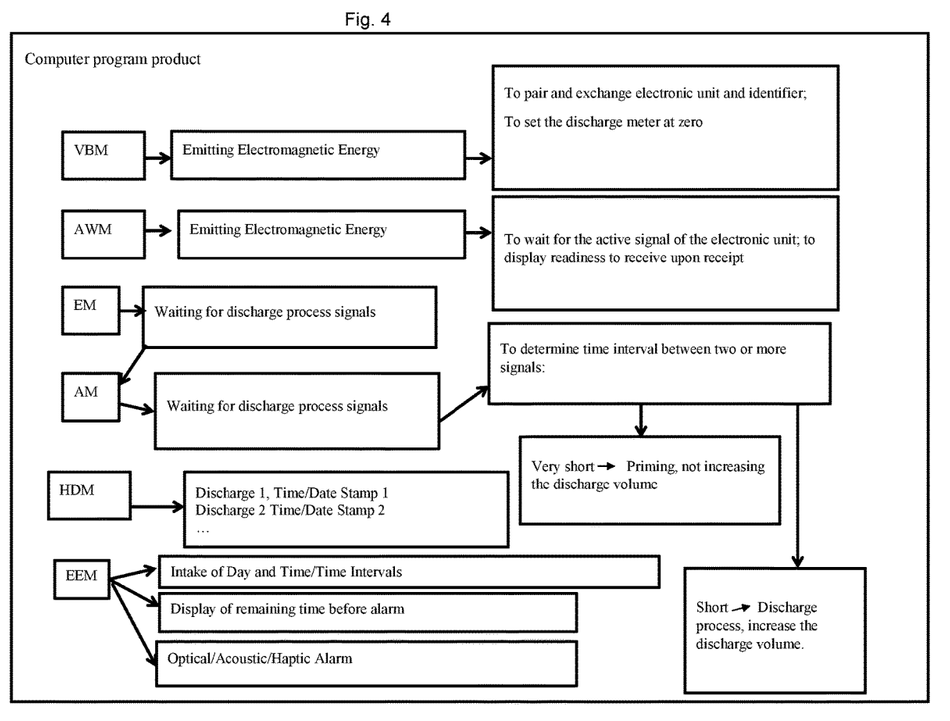
FIG. 4 shows the computer program product in cooperation with an electronic unit in the pump cap or the use with the personal digital assistant, on which the computer program product is executed.

The computer program product running on the personal digital assistant PDA in preparation mode VBM causes the pairing of a respective electronic unit 12 in (an inlay or directly in) the pump cap 10 with the personal digital assistant PDA. For this purpose, the user starts the preparation mode of the computer program product and brings the personal digital assistant PDA into the spatial proximity of the pump cap 10 comprising the electronic unit 12. In the preparation mode VBM of the computer program product, this initiates the emission of electromagnetic energy according to the NFC-standard ISO/IEC 14443 A and B or ISO/IEC 15693 via the NFC-functionality (coils, control electronic, appropriate NFC-control software (=NFC protocol stack) in the processor operating system) of the personal digital assistant PDA. As soon as the electronic unit 12 receives sufficient electromagnetic energy via its coil antennae 12a from the antenna in the personal digital assistant PDA, the electronic unit 12 is activated and reacts with the confirmation signal transmitted by its coil antenna 12a. Now, the personal digital assistant PDA transmits, for example an (alphanumeric) multi-digit individualized identification, which is received by the electronic unit 12 via the antenna 12a and is saved in a non-volatile storage unit of the chip of the electronic unit 12, the EEPROM, which is not shown in greater detail here.

Alternatively, it is also possible that after the activation of the electronic unit 12, said unit also transmits from the memory unit of the chip a multi-digit individualized identification stored there, for example an alphanumerical one, via the antenna 12a to the personal digital assistant PDA.

In both variants it is achieved that, on the one hand, the personal digital assistant PDA and, on the other hand, the electronic unit 12 in the pump cap 10, are adjusted to each other. Here, during the later receipt of discharge processes from the pharmaceutical container 18 from signals reflecting the activation of the pump cap 10, the computer program product can reliably allocate these signals exclusively to this very assembly, and not to any other one, and process them accordingly. Additionally, a discharge meter is reset to zero.

In order to record with the personal digital assistant PDA and the simultaneously running computer program product, any signals reflecting discharge processes from the pharmaceutical container 18 by activation of the pump cap 10 and to allow displaying them on the monitor of the personal digital assistant PDA, in a wake-up mode AWM, the electronic unit 12 is activated (located in an inlay or directly in) the pump cap 10.

For this purpose, the user starts the computer program product and brings the personal digital assistant PDA into the spatial proximity of the pump cap 10 comprising the electronic unit 12. In the preparation mode VBM of the computer program product, it initiates the transmission of electromagnetic energy according to the NFC-standard ISO/IEC 14443 A and B or in ISO/IEC 15693 via the NFC-functionality (coils, control electronic, appropriate NFC-control software (=NFC protocol stack) in the processor operating system) of the personal digital assistant PDA. As soon as the electronic unit 12 receives sufficient electromagnetic energy via its coil antenna 12a from the antenna of the personal digital assistant PDA, the electronic unit 12 is activated. Once the transmitted electromagnetic energy is sufficient, the electronic unit 12 transmits a brief "active signal" together with its individualized identification to the personal digital assistant PDA. This occurs commonly within one or two seconds after the user has brought the personal digital assistant PDA into spatial proximity of the pump cap 10 comprising the electronic unit 12. The receipt of the "active signal" and thus the readiness of the personal digital assistant PDA to detect discharge processes from the pharmaceutical container 18 by signals reflecting the activation of the pump cap 10, processing and ability to display these signals on the monitor of the personal digital assistant PDA are indicated by the computer program product by an appropriate acoustic or visual message on the monitor of the personal digital assistant PDA.

In the next step of the computer program product, the personal digital assistant PDA is kept in receiver mode EM. In this receiver mode EM, the computer program product waits for the user operating the pump cap 10 such that the electronic unit 12 transmits via its coil antenna 12a signals which reflect discharge processes from the pharmaceutical container 18 by activating the pump cap 10.

In order to prevent that the counting of the discharge processes is dependent on the operation of the pump cap 10 by the user, all activations of the pump cap 10 are transmitted by the electronic unit 12 to the personal digital assistant PDA. The computer program product however evaluates how much time elapses between two activations of the pump cap 10. If very short intervals (approximately 1-4 seconds) are signalized between two or more activations of the pump cap 10 by the electronic unit 12, this shall be categorized by the computer program product as a so-called priming of the pharmaceutical container 18;

the computer program product abstains from increasing the discharge meter but shows the present status on the monitor of the personal digital assistant PDA.

If two activations of the pump cap 10 are signaled by the electronic unit 12 in short intervals (approximately 4-10 seconds) to the personal digital assistant PDA, this is categorized by the computer program product as two discharge events (one discharge process for each nostril of the user); the computer program product accordingly increases the discharge meter and shows the present status on the monitor of the personal digital assistant PDA. Additionally, this number of discharge processes is saved together with a current date/time stamp in the memory of the personal digital assistant PDA for later use.

In the present case, a differentiation is described between the so-called priming of the pharmaceutical container 18 and two discharge processes using different temporal intervals between two activations of the pump cap 10. In one variant, not shown in greater detail, it is provided in case of two activations of the pump cap 10, regardless of the time interval, to increase in the computer program product the discharge meter accordingly and to display the current status on the monitor of the personal digital assistant PDA. If more than two activations of the pump cap 10 are signaled within a predetermined period, e.g., 5-15 seconds, to the computer program product, in another variant, not shown in greater detail either, the discharge meter in the computer program product is increased by two and the current status is displayed on the monitor of the personal digital assistant PDA.

Another variant provides, after the pairing of a respective electronic unit 12 (in an inlay or directly in) the pump cap 10 with the personal digital assistant PDA, in a first step to prompt the user for priming using a message on the monitor of the personal digital assistant PDA. Here, the signalized interval is recorded and saved in the computer program product for comparison of the signal progression for later activations of the pump cap 10. In a second step, using a message on the monitor of the personal digital assistant PDA, then the user is prompted to execute two discharge processes (one discharge event for each nostril of the user). Here, the signaled interval is also recorded and saved in the computer program product for comparison of the signal progression in case of later operation of the pump cap 10.

In a subsequent operation of the pump cap 10, the temporal progression of the activations of the pump cap 10 signaled is compared to the saved progressions. Depending on the categorized activations of the pump cap 10, then the computer program product increases the discharge meter accordingly by two (or not, if the operations were categorized as priming) and the current status is displayed on the monitor of the personal digital assistant PDA.

In addition to the above-described functionalities of the computer program product, here, a history display mode HDM is provided, which displays the discharge events counted since the most recent pairing of the respective electronic unit 12 of the pump cap 10 with the personal digital assistant PDA, respectively provided with time/date stamp, on the monitor of the personal digital assistant PDA. For this purpose, the discharge processes saved in the personal digital assistant PDA are read from the memory of the personal digital assistant PDA together with the respective date/time stamp and processed into a list or graph, and indicated for example along a timeline.

Furthermore, an application reminder mode EEM is provided, in which the user can enter one or more times of day or intervals at which the user shall respectively perform the next administration. It is displayed on the monitor of the personal digital assistant PDA how much time remains until the next administration. At the specified point of time of administration, the personal digital assistant PDA then triggers an optic and/or acoustic and/or haptic alarm.

The presently described functionalities of the computer program product can also be integrated in a computer program product (app), which furthermore allows a number of other functions and options for the user. For example, various symptoms can be documented in their severity and frequency and perhaps correlated to the administration cycle of the medication.

The above-described variants as well as their design and operating aspects serve only for the better understanding of the structure, the functionality, and the features; they have no limiting effect upon the disclosure, for example to the design examples. The figures are partially schematic, with essential features and functions being shown sometimes considerably enlarged in order to illustrate functions, effects, technical designs, and features. Here, each functionality, each principle, each technical feature, and each characteristic disclosed in the figures or the text can be combined with all claims, all features in the text, and in the other figures, other functionalities, principles, technical designs, and features included in this disclosure or resulting therefrom, in a free and arbitrary fashion such that all possible combinations of the described variants shall be included, here.

Here, combinations between all individual designs in the text are also possible; this means in every section of the description, in the claims, and also combinations between different variants in the text, in the claims and the figures. The claims shall also not be considered limited to their disclosure and thus shall not exclude any potential combinations of all features shown. All disclosed features are explicitly also disclosed individually and in combination with all other characteristics.

The invention claimed is:

1. A pharmaceutical container comprising:
   a. a pump cap fitted to the pharmaceutical container and configured for actuation by a user relative to the pharmaceutical container to release a portion of the pharmaceutical container contents; and
   b. an electronic unit attached to the pump cap, the electronic unit comprising a transmitter configured to generate a wireless reporting signal, the electronic unit also configured to receive wireless signals in the form of instructions, wherein wireless signals from and to the electronic unit are, respectively, received and generated by one or more electronic appliance(s) in the form of a personal digital assistant, wherein the electronic unit is a chip module comprising an antenna designed as a coil or dipole for contactless, automated generation and/or receipt of data in or out of the chip; and
   c. a wrap having an outside diameter smaller than an inside diameter of the pump cap and a passage opening for a medicine discharge connection piece for the pharmaceutical container, wherein the wrap is fitted to the antenna,
   wherein the one or more actuations of the pump cap by the user results in the wireless reporting signal being transmitted.

2. The pharmaceutical container of claim 1, wherein the generated data comprises a personalized identifier for pairing the electronic unit with the personal digital assistant and signals reported by actuation of the pump cap.

3. The pharmaceutical container of claim 2, wherein the electronic unit is integrated into the pump cap and receives its operational energy from the personal digital assistant.

4. The pharmaceutical container of claim 3, wherein the electronic unit is adapted to receive operational energy from the personal digital assistant and the personal digital assistant is selected from the group consisting of a mobile phone, a cordless phone, a smart phone, a smart watch, a tablet computer, a notebook computer and a computer.

5. The pharmaceutical container of claim 1, wherein the transmitter is adapted to transmit the reporting signals via near-field communication.

6. The pharmaceutical container of claim 1, further comprising:
   a sensor comprising a switch adapted to record a discharge, the switch being activated upon actuation of the pump cap to cause a discharge process.

7. A pharmaceutical container comprising:
   a. a pump cap actuated relative to the pharmaceutical container by a user to release contents of the container;
   b. a transceiver attached to the pump cap, the transceiver generating wireless signals upon one or more actuations of the pump cap, the transceiver also receiving wireless signals from a personal digital assistant; and
   c. a wrap having an outside diameter smaller than an inside diameter of the pump cap and a passage opening for a medicine discharge connection piece for the pharmaceutical container, wherein the wrap is fitted to an antenna that is a planar ring coil or a dipole.

8. The pharmaceutical container of claim 7, wherein the transceiver is part of a chip module comprising an antenna designed as a coil or dipole for the wireless, automated generation and retrieval of data, wherein the data comprises a personalized identifier for pairing the chip module with a computer program product in the personal digital assistant and/or the retrieved data comprises the signals reported by the activation of the pump cap.

9. The pharmaceutical container of claim 7, wherein the transceiver is integrated in the wrap and receives its operational energy from the personal digital assistant.

10. The pharmaceutical container of claim 9, wherein the personal digital assistant is selected from the group consisting of a mobile phone, a cordless phone, a smart phone, a smart watch, a tablet computer, a notebook computer and a computer.

11. The pharmaceutical container of claim 7, further comprising a sensor comprising a switch adapted to record actuation of the pump cap, the switch comprising two electrical contacts adapted and arranged in a way that they are electrically bridged via a component in the pharmaceutical container.

12. The pharmaceutical container of claim 7, wherein the wrap comprises one or more layers of a material selected from the group consisting of plastic, paper, plastic coated paper and paper stuffed with plastic.

13. The pharmaceutical container of claim 12 wherein the plastic is one or more of polyethylene, polyvinyl chloride, polyvinyl chloride-acetate-copolymer, polyethylene terephthalate, polyethylene terephthalate glycol-modified, polyethylene naphthalate, acrylonitrile-Butadiene-Styrene-Co-polymers, polyvinyl butyral, polymethyl-methacrylate, polyimide, polyvinyl alcohol, polystyrene, polyvinyl phenol, polyethylene, polypropylene, polycarbonate or their foil derivatives with a thickness of at least 75 μm or more.

14. The pharmaceutical container of claim 7, wherein the contents of the container is azelastine hydrochloride and fluticasone propionate.

15. A non-transitory computer program product adapted and programmed to provide operational energy to the pharmaceutical container of claim 7 by way of a personal digital assistant and to record the discharge process of the pharmaceutical container, comprising:
   a. a preparatory mode to produce a pairing of each electronic unit in an inlay in the pump cap with the personal digital assistant,
   b. a wake-up mode to activate the electronic unit in the inlay and/or pump cap,
   c. a receiver mode to wait for activation by the pump cap user in order for the electronic unit to transmit signals that report the discharge process from the pharmaceutical container by retrieval, and
   d. an evaluation mode to measure elapsed periods between successive pump cap activations and to categorize different incidents based on the elapsed period.

16. The non-transitory computer program product of claim 15, wherein
   a. the preparation mode of the computer program product is adapted and programmed to produce radiation of electromagnetic energy via the personal digital assistant so that the electronic unit receives electromagnetic energy of the antenna in the personal digital assistant via its coil antenna, through which the electronic unit is activated and reacts with one of the activation signals transmitted via its coil antenna;
   b. of the computer program product is adapted and programmed to transmit an individualized identification that can be received by the electronic units through their antennae and be stored in the electronic unit; or the electronic unit sends out one of its stored individualized identifications to the personal digital assistant via its antennae, and
   c. of the computer program product is adapted and programmed to set a discharge meter to zero.

17. The non-transitory computer program product of claim 16, wherein
   a. the wake-up mode of the computer product is adapted and programmed to cause the radiation of electromagnetic energy through the personal digital assistant so that the electronic unit receives electromagnetic energy of the antenna in the personal digital assistant via its coil antenna and transmits an active signal as well as its individualized identification to the personal digital assistant; and
   b. of the computer program adapted and programmed to emit audio and/or visual displays after receiving an active signal via the personal digital assistant to specify the readiness of the personal digital assistant to record the discharge process from the pharmaceutical container through the reporting signals caused by activating the pump cap and to process the personal digital assistant and/or be able to display the same on the screen.

18. The non-transitory computer program product of claim 17, wherein
   a. the evaluation mode of the computer program product is adapted and programmed to categorize, within a very short time interval, two or more pump cap activations signaled by the electronic unit as priming of the pharmaceutical container and not to increase the discharge meter;
   b. of the computer program product is adapted and programmed to categorize, within a very short time interval, two or more pump cap activations signaled by the electronic unit as two discharge processes and to increase the discharge meter accordingly; and
   c. of the computer program product stores the number of this discharge process along with a date and time stamp in the personal digital assistant.

19. The non-transitory computer program product of claim 18, wherein
   a. the computer program product is adapted and programmed to present the numbered discharge processes since the last pairing of each pump cap's electronic unit with the personal digital assistant in a history display mode, each provided with the time and date stamp on the screen of the personal digital assistant, and/or
   b. the computer program product in an application reminder mode adapted and programmed to enable the user to enter one or more day-time or time intervals into the personal digital assistant under which additional intakes should be performed, wherein the computer program product is adapted and programmed in a way that the period still remaining before the next intake is displayed on the screen of the person digital assistant and/or
   the computer program product is adapted and programmed to raise an alarm, optically, acoustically, and/or haptically, at a specified time of the personal digital assist.

* * * * *